(12) United States Patent
Neumann et al.

(10) Patent No.: US 7,572,230 B2
(45) Date of Patent: Aug. 11, 2009

(54) METHOD FOR THE PRESENTATION OF INFORMATION CONCERNING VARIATIONS OF THE PERFUSION

(75) Inventors: Rolf Neumann, Calw (DE); Andreas Bindszus, Böblingen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 483 days.

(21) Appl. No.: 10/531,413

(22) PCT Filed: Oct. 2, 2003

(86) PCT No.: PCT/IB03/04354

§ 371 (c)(1),
(2), (4) Date: Apr. 15, 2005

(87) PCT Pub. No.: WO2004/034898

PCT Pub. Date: Apr. 29, 2004

(65) Prior Publication Data

US 2006/0167362 A1 Jul. 27, 2006

(30) Foreign Application Priority Data

Oct. 15, 2002 (DE) ............... 102 47 984

(51) Int. Cl.
*A61B 5/02* (2006.01)
*G08B 23/00* (2006.01)
(52) U.S. Cl. ............ 600/504; 600/507; 600/483; 340/573.1
(58) Field of Classification Search ......... 600/300–301, 600/310, 322–324, 326, 368, 363, 483–504, 600/523, 481; 340/573.1; 345/150, 133, 345/700, 864; 128/709, 710, 712, 920–925
See application file for complete search history.

(56) References Cited

U.S. PATENT DOCUMENTS

| | | | | |
|---|---|---|---|---|
| 4,109,643 A | * | 8/1978 | Bond et al. | 600/479 |
| 4,484,584 A | * | 11/1984 | Uemura | 600/493 |
| 4,867,165 A | * | 9/1989 | Noller et al. | 600/328 |
| 4,869,253 A | * | 9/1989 | Craig et al. | 600/323 |
| 5,103,828 A | * | 4/1992 | Sramek | 600/481 |
| 5,203,342 A | * | 4/1993 | Sakai | 600/504 |
| 5,275,159 A | * | 1/1994 | Griebel | 600/324 |
| 5,297,548 A | * | 3/1994 | Pologe | 600/310 |
| 5,299,570 A | * | 4/1994 | Hatschek | 600/479 |

(Continued)

FOREIGN PATENT DOCUMENTS

CH     559 034     2/1975

(Continued)

*Primary Examiner*—Charles A Marmor, II
*Assistant Examiner*—Navin Natnithithadha

(57) ABSTRACT

The invention relates to a method for the presentation of information concerning variations of the arterial filling with blood (perfusion) of organs of living beings on the user surface (10) of a display screen, in which method the data required for the presentation (perfusion index) is derived, using an algorithm, from measuring values of a non-invasive photometric measuring process for determining the arterial oxygen saturation of the blood. The invention is characterized in that a first perfusion index is defined as a reference value and the subsequent perfusion indices are determined as relative deviations with respect to the reference value, said relative deviations being presented in the form of analog, graphic elements (42, 44) on the user surface (10) as information concerning the 10 variations of the perfusion.

11 Claims, 5 Drawing Sheets

U.S. PATENT DOCUMENTS

Figure 1:

| | | | | |
|---|---|---|---|---|
| 5,438,983 | A * | 8/1995 | Falcone | 600/301 |
| 5,680,857 | A * | 10/1997 | Pelikan et al. | 600/323 |
| 5,685,301 | A * | 11/1997 | Klomhaus | 600/366 |
| 5,690,104 | A * | 11/1997 | Kanemoto et al. | 600/323 |
| 5,810,723 | A * | 9/1998 | Aldrich | 600/322 |
| 5,830,150 | A * | 11/1998 | Palmer et al. | 600/523 |
| 5,860,918 | A * | 1/1999 | Schradi et al. | 600/300 |
| 5,912,656 | A * | 6/1999 | Tham et al. | 345/418 |
| 6,083,206 | A * | 7/2000 | Molko | 604/253 |
| 6,122,535 | A * | 9/2000 | Kaestle et al. | 600/322 |
| 6,177,923 | B1 | 1/2001 | Arenson et al. | |
| 6,178,342 | B1 * | 1/2001 | Borgos et al. | 600/322 |
| 6,196,974 | B1 * | 3/2001 | Miwa | 600/490 |
| 6,322,516 | B1 * | 11/2001 | Masuda et al. | 600/493 |
| 6,415,166 | B1 * | 7/2002 | Van Hoy et al. | 600/323 |
| 6,501,974 | B2 * | 12/2002 | Huiku | 600/331 |
| 6,584,336 | B1 * | 6/2003 | Ali et al. | 600/323 |
| 6,587,701 | B1 * | 7/2003 | Stranc et al. | 600/310 |
| 6,631,281 | B1 * | 10/2003 | Kastle | 600/336 |
| 6,658,276 | B2 * | 12/2003 | Kianl et al. | 600/322 |
| 6,770,028 | B1 * | 8/2004 | Ali et al. | 600/300 |
| 6,898,462 | B2 * | 5/2005 | Rock et al. | 607/4 |
| 6,939,307 | B1 * | 9/2005 | Dunlop | 600/504 |
| 6,985,762 | B2 * | 1/2006 | Brashears et al. | 600/323 |
| 2002/0147390 | A1 * | 10/2002 | Markis et al. | 600/301 |
| 2002/0161291 | A1 * | 10/2002 | Kianl et al. | 600/324 |
| 2003/0197679 | A1 * | 10/2003 | Ali et al. | 345/158 |
| 2003/0212437 | A1 * | 11/2003 | Rock et al. | 607/9 |
| 2004/0102687 | A1 * | 5/2004 | Brashears et al. | 600/323 |
| 2004/0204635 | A1 * | 10/2004 | Scharf et al. | 600/323 |
| 2005/0021110 | A1 * | 1/2005 | Maschke et al. | 607/88 |
| 2005/0055243 | A1 * | 3/2005 | Arndt et al. | 705/2 |
| 2005/0080348 | A1 * | 4/2005 | Stahmann et al. | 600/529 |
| 2005/0085738 | A1 * | 4/2005 | Stahmann et al. | 600/529 |
| 2005/0102165 | A1 * | 5/2005 | Oshita et al. | 705/3 |
| 2005/0115561 | A1 * | 6/2005 | Stahmann et al. | 128/200.24 |
| 2005/0177096 | A1 * | 8/2005 | Bollish et al. | 604/65 |
| 2006/0149154 | A1 * | 7/2006 | Stephens et al. | 600/504 |
| 2006/0167362 | A1 * | 7/2006 | Neumann et al. | 600/504 |
| 2006/0189871 | A1 * | 8/2006 | Al-Ali et al. | 600/476 |
| 2006/0192667 | A1 * | 8/2006 | Al-Ali | 340/511 |
| 2006/0220881 | A1 * | 10/2006 | Al-Ali et al. | 340/573.1 |
| 2006/0226992 | A1 * | 10/2006 | Al-Ali et al. | 340/573.1 |
| 2006/0238358 | A1 * | 10/2006 | Al-Ali et al. | 340/573.1 |

FOREIGN PATENT DOCUMENTS

| | | |
|---|---|---|
| EP | 0 194 105 A2 | 9/1986 |
| EP | 0 261 787 A1 | 3/1988 |
| EP | 587009 * | 3/1994 |
| EP | 0 807 402 A1 | 11/1997 |

* cited by examiner

METHOD FOR THE PRESENTATION OF INFORMATION CONCERNING VARIATIONS OF THE PERFUSION

The following relates to a method for the presentation of information concerning variations of the perfusion, to a method for the presentation of the quality of the measuring values (signal quality) acquired during a photometric measuring process, and to a device for carrying out the method.

As is known, in the field of patient monitoring special patient data such as, for example, perfusion, oxygen saturation of the arterial blood ($SPO_2$ value), ECG curves and the like are important for the evaluation of the condition of a patient.

Information as regards the perfusion can be derived only indirectly in normal practice. To this end, the clinical staff can fall back on measuring values resulting from the measurement of the oxygen saturation of the arterial blood.

The measurement of the arterial oxygen saturation of the blood or the arterial hemoglobin is usually performed continuously in a non-invasive manner by means of a photometric measuring process, that is, the so-called pulsoximetry. A peripheral part of the body, usually a finger, is then irradiated by means of a sensor. The sensor usually comprises two light sources for the emission of light and a corresponding photodetector for the measurement of the light absorption.

Pulsoximetry is based on two principles. On the one hand, the oxygen-enriched hemoglobin (oxyhemoglobin) and the oxygen-reduced hemoglobin (desoxyhemoglobin) differ as regards their ability to absorb red and infrared light (spectrophotometry) and on the other hand the amount of arterial blood in the tissue changes, and hence also the absorption of light by this blood, during the pulse (plethysmography). A pulsoximeter determines the $SPO_2$ value by emitting red and infrared light and by measuring the variations of the light absorption during the pulse cycle.

Whereas the clinical staff is presented with the oxygen saturation of the blood, that is, the $SPO_2$ value, in the form of a numerical value, for information concerning the perfusion the staff has to take recourse to an interpretation of the plethysmography curve which is presented in the context of the pulsoximetry; this curve also shows inter alia the variation of the volume of a part of the body which is induced by the perfusion.

Because the perfusion is a clinically relevant parameter which is used, for example, to signal the changing of physiological factors, the effect of anesthesia or the like, this way of deriving information concerning the perfusion is found to be very detrimental.

On the one hand, the read-out accuracy is limited as the information has to be read from a curve which is not especially conceived for this purpose, meaning that this information has to be estimated, whereas on the other hand the amplification must be invariable for the presentation of the curve, making an evaluation of the shape of the curve practically impossible in the case of a very low perfusion. Moreover, a change of the curve amplitude in the plethysmogram is also dependent on the oxygen saturation and not only on the amount of blood flowing into the part of the body, for example, a finger.

U.S. Pat. No. 4,867,165 A1 discloses a method for determining the perfusion whereby the perfusion can be quantified. To this end, a so-called perfusion index is determined from measuring values of the pulsoximetry process by means of an algorithm. It has been found to be a drawback of this method, however, that it yields absolute values only so that the detection of a variation of the perfusion by the clinical staff must take place by continuous observation and comparison of numerical values.

It is an object of the invention to mitigate this problem by way of a method for the presentation of information concerning variations of the perfusion, thus facilitating the reading out of this information while avoiding said drawbacks.

In respect of the method this object is achieved by a method for the presentation of information concerning variations of the arterial filling with blood of organs of living beings on the user surface of a display unit, in which method the data required for the presentation is determined, using an algorithm, from measuring values produced by a non-invasive photometric measuring process for determining the arterial oxygen saturation of the blood, wherein a first perfusion index is defined as a reference value and the subsequent perfusion indices are determined as relative deviations with respect to the reference value, said relative deviations being presented as information concerning the variations of the perfusion on the user surface. In respect of the device it is achieved by a device, comprising a pulsoximeter for determining arterial $O_2$ saturation and for calculating perfusion index in order to determine information concerning variation of the perfusion, means for detection of interference signals, and for estimating the quality of the measuring values acquired and the information concerning a variation of the perfusion, and means for presenting the information.

Further features are disclosed. A method is disclosed of determining the quality of the measuring values (signal quality) derived by a photonic measuring process, notably in combination with a method as disclosed herein. The signal quality is determined by a single one or a combination of the following variables: saturation-independent perfusion index, transmission factor, extent of ambient disturbances (such as stray light, EM radiation and the like), shape of the PLETH signal, and strength and/or duration of artifacts. A method is disclosed of determining the quality of the measuring values derived by a photometric measuring process, wherein the signal quality is determined b the modulation factor (AC/DC) of one or more wavelengths in combination with one or more of the following variables: saturation-independent perfusion index transmission factor extent of ambient disturbances, such as stray light, EM radiation, and the like shape of the PLETH signal strength and/or duration of artifacts. A method is disclosed of presenting the quality of the measuring values (signal quality) derived by the aforementioned photometric measuring process, wherein this information is graphically presented on the user surface by way of different coloring of icons and/or background areas, the coloring depending on said quality. In some embodiments, the icons are identical to the graphic elements used for the presentation of the perfusion. In some embodiments, the icons are independent graphic elements.

The invention is based on the recognition of the fact that information represented by autonomous graphic elements can be observed faster and simpler than information that has to be derived by interpretation of curves or comparison of several numerical values.

In accordance with the invention, the numerical data (perfusion index) required for the graphic presentation of the variations of the perfusion is determined continuously from measuring values of the photometric measuring process while using an algorithm. A first perfusion index is defined as a reference value and the relative deviations of the subsequent perfusion indices are determined in relation to this reference value. These relative deviations are represented by analog graphic elements on the user surface of the display screen as information concerning the variation of the perfusion.

Thus, it is simply possible to read out the relative variation of the perfusion, which is presented in the form of analog graphic elements. Such a representation is very advantageous, because the clinical staff is presented with significant and ready-for-use information concerning the variation of the perfusion. Interpretation on the basis of the plethysmography curve or by continuous observation and comparison of numerical values is no longer necessary. Moreover, the size of presentation of the plethysmography curve can now be automatically adapted to the signal, thus facilitating interpretation of the curve characteristic.

Preferably, the reference value is automatically determined at the beginning of the photometric measuring process.

The instant for determining the reference value, however, can also be chosen at will by the clinical staff. It is thus ensured that a negative effect on the reference value, for example, due to a temporary state of shock of the patient or the like, can be precluded by way of a suitable choice of the instant for determining the reference value.

For reasons of flexibility, for example, for the comparison of two reference values of a patient which have been determined at different instants, such values can be stored on a memory chip.

In order to enable adjustment of the size of the graphic element and hence of the presentation of the information concerning variations of the perfusion, the reference value as well as the subsequent perfusion indices can be normalized or scaled with a factor.

Preferably, this factor is individually adjustable. The individual adjustability offers the advantage that the representation can be readjusted in dependence on a relevant situation, for example, also during an operation, so that an optimum presentation of the information concerning variations of the perfusion is always ensured.

In order to ensure a clear, readily recognizable presentation of the information, the information concerning variations of the perfusion is presented in the form of bar elements.

The relative variations of the perfusion are preferably represented by way of different lengths of the bars. The use of different bar lengths for the representation of the relative variation has been found to be advantageous, because it ensures in a simple manner a fast optical and intuitive recognition of a change of information by the clinical staff.

In order to facilitate the recognition of critical variations of the perfusion there is provided an upper alarm limit and a lower alarm limit, each of which is individually adjustable. When a critical value is reached, that is, when the adjusted alarm limits are exceeded, such an event can then be accentuated by means of an optical and/or acoustic signal.

Preferably, the quality of the measuring values (signal quality) acquired during the photometric measuring process is presented on the user surface of the display screen by way of a different color of icons or background areas, that is, the color green for everything in order, yellow for dubious and red for poor. The estimation of the signal quality can be performed, for example, by evaluation of a combination of various parameters such as, for example, transmission level, interference level, artifact level, signal waveform, perfusion index or the like. The additional presentation of the signal quality is of major importance to the clinical staff, because it enables an evaluation of the measuring values derived from pulsoximetry as well as an evaluation of the information concerning the variations of the perfusion. Moreover, the coloring ensures intuitive observation, which in turn substantially simplifies the interpretation of the indicated signal quality.

Preferably, the same graphic elements are used for the presentation of the variations of the perfusion and for the presentation of the signal quality. Thus, a bar element provided for the presentation of the variation of the perfusion may at the same time be colored, that is, green for the signal quality o.k., yellow for a reduced signal quality, or red for a poor signal quality. This form of presentation, where the icons for the presentation of the signal quality are identical to the graphic elements for the presentation of the variations of the perfusion, has been found to be advantageous, because it results in a space-saving display format. A further space-saving possibility for presentation consists in that a background area, for example, the background of the bar elements, the plethysmography curve or also the background of the numerical display for the oxygen saturation, is characterized by a corresponding color. Coloring of other elements, for example, of the plethysmography curve itself, is also feasible.

However, it is also possible to present the icons as independent graphic elements, notably as a segment or bar representation, as color-encoded surface elements, or in the form of three circular elements arranged like a traffic light.

The device for carrying out the method includes a pulsoximeter for determining the arterial $O_2$ saturation and for calculating the perfusion index for the determination of the information concerning the variation of the perfusion, means for detecting interference signals, notably motion artifacts, and for estimating the quality of the acquired measuring values and hence the information concerning a variation of the perfusion, and means for displaying the information.

Further advantages and feasible applications of the present invention are disclosed in the following description in conjunction with the embodiment which is shown in the drawing.

Figure 2:
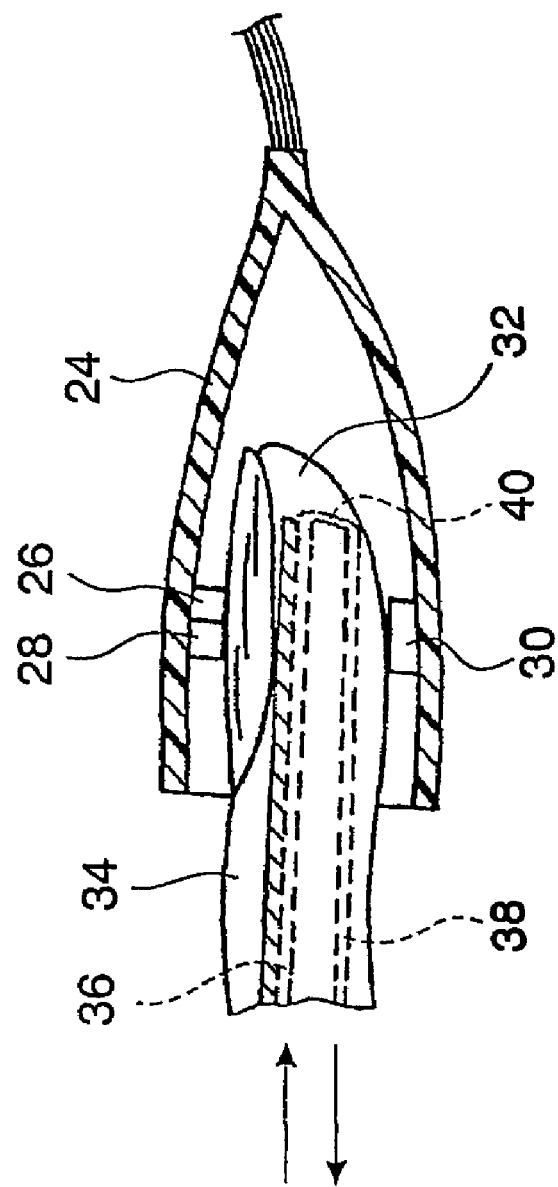
Figure 3:
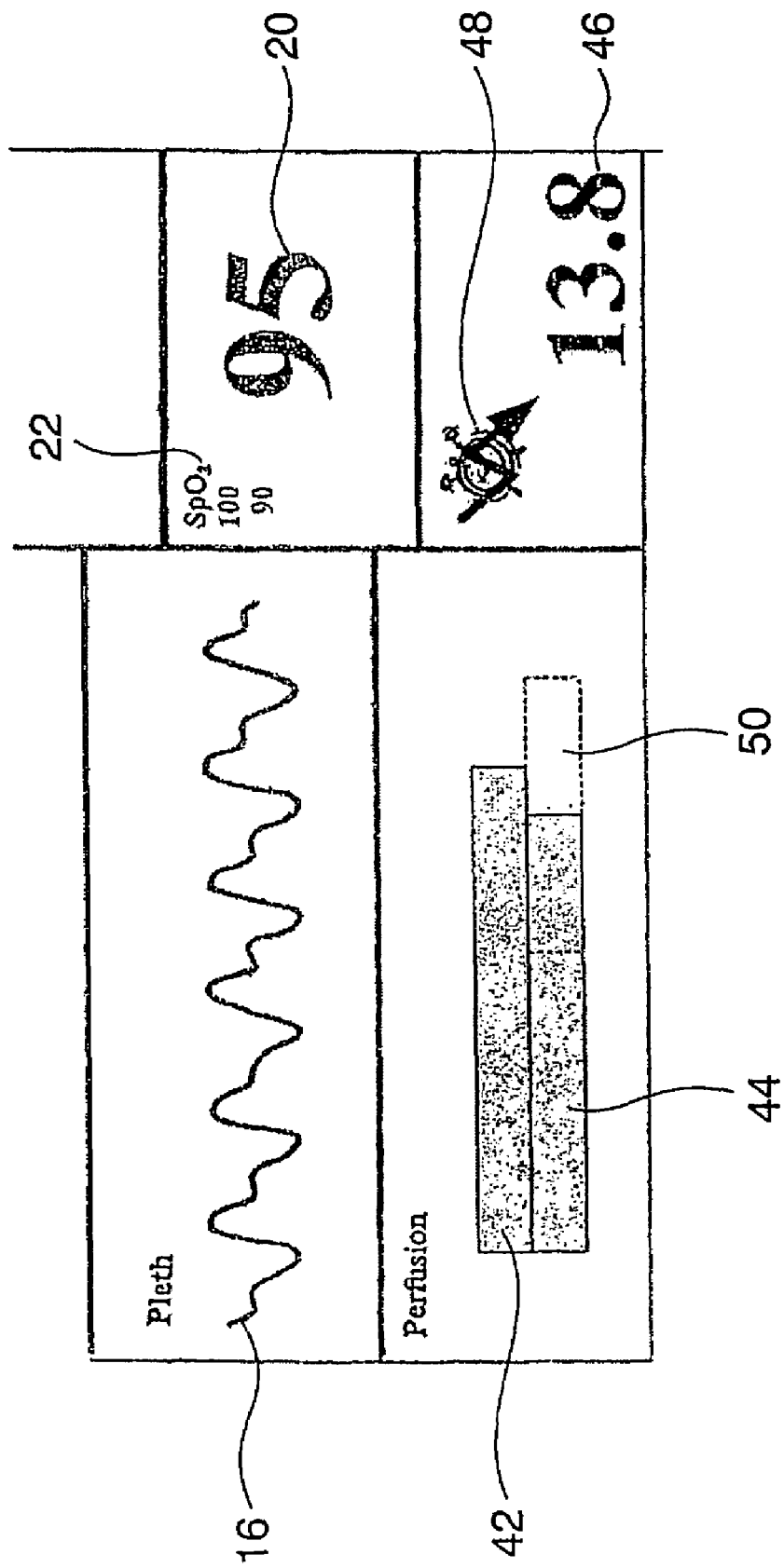
Figure 4:
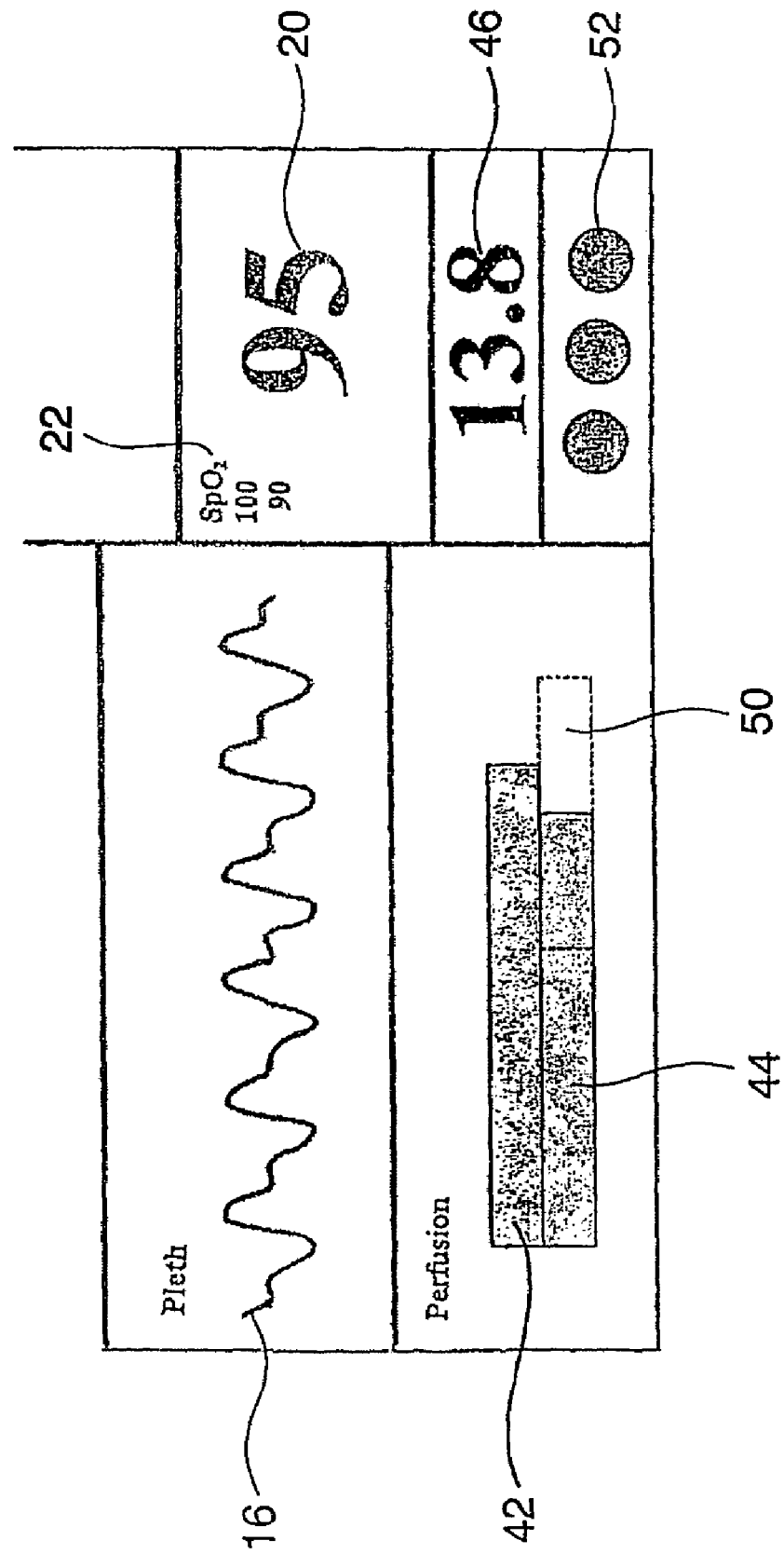
Figure 5:
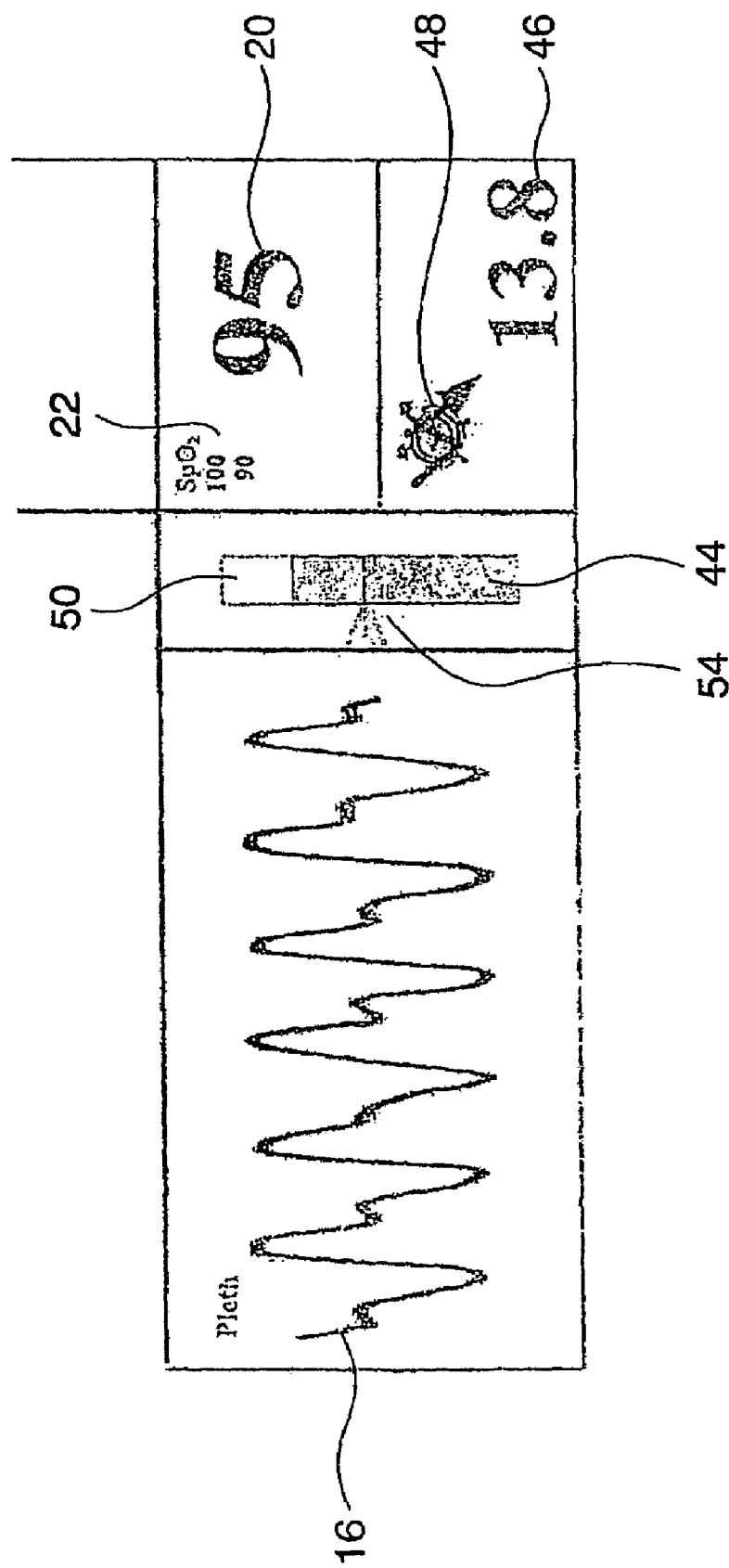

The invention is described more or less diagrammatically hereinafter on the basis of an embodiment as shown in the drawing. Therein:

FIG. 1 is a diagrammatic representation of a user surface of a display screen as used in the field of patient monitoring, FIG. 2 shows a measuring cap which is fitted on the tip of a finger and comprises two light-emitting diodes and a photoreceiver, FIG. 3 shows a part of a further user surface with graphic elements for the presentation of the perfusion, FIG. 4 shows a part of a user surface with graphic elements for the presentation of the perfusion and independent graphic elements for the presentation of the signal quality, and FIG. 5 shows a further part of a user surface with graphic elements for the presentation of the variation of the perfusion.

For a better understanding of the invention a brief description will first be given of the procedures used thus far for the determination of the perfusion of a patient.

FIG. 1 shows a typical user surface 10 as used in the field of patient monitoring. The Figure shows inter alia a plurality of dynamically varying patient data, such as an ECG (electrocardiography) curve (derivative I) 12, a further ECG curve (derivative II) 14, a plethysmography curve 16 as well as a $CO_2$ respiration curve 18. To the right of the real-time curves 12, 14, 16 and 18 the associated physiological values are displayed in numerical form. For example, to the right of the plethysmography curve 16 the current value of the oxygen saturation of the arterial blood ($SPO_2$ value) 20 is shown with associated alarm limits 22.

With regard to the perfusion to be monitored, thus far the plethysmography curve 16 was observed by the clinical staff in order to derive information as regards the current perfusion by interpretation of the varying curve amplitude.

As is known, the plethysmography curve 16 is determined by means of a photometric measuring process, that is, the so-called pulsoximetry.

Pulsoximetry is a spectrophotometric method for the non-invasive determination of the arterial oxygen saturation of the blood. To this end, use is made of a measuring cap 24 as shown in FIG. 2, which cap comprises two light-emitting diodes 26, 28 and a photoreceiver 30 and is fitted on the tip 32 of a finger of the patient to be monitored. The arteries 36 and veins 38 extending in the tissue 34 and the capillaries 40 present between the arteries 36 and veins 38 are denoted by dashed lines. The light-emitting diodes 26 and 28 emit light of different wavelength, for example, 660 nm and 950 nm, to the photoreceiver 30. The photoreceiver 30 measures the intensity variation of the light which is due to a variation of an arterial blood volume and converts this information into a current signal which serves inter alia to present the plethysmography curve 16 on the user surface 10. Since photometric measuring methods are well known, for the sake of simplicity the measuring method will not be shown or elaborated further.

In order to enable direct representation of the variations of the perfusion of a patient, a known algorithm is used to determine the so-called perfusion index from the measuring values continuously produced by pulsoximetry. After a first perfusion index has been defined as a reference value, the relative deviations of the subsequently calculated perfusion indices are determined relative to the reference value. Such relative deviations then serve as information concerning the variation of the perfusion and are presented on the user surface 10 in the form of graphic elements.

Because artifacts due to optical disturbances or motion of the patient are recognized prior to the calculation of the perfusion index and filtered by the algorithm, it is ensured that the information displayed in respect of the variation of the perfusion is highly accurate.

For reasons of simplicity, the algorithms necessary for the calculation of the perfusion indices and the presentation of the graphic elements on the user surface 10 will not be elaborated further herein.

FIG. 3 shows a part of a further user surface 10 as used in the field of patient monitoring. In addition to the plethysmography curve 16 and the current $SPO_2$ value 20 with associated alarm limits 22, information concerning the variation of the perfusion is also shown. The information is represented by means of two bar elements 42, 44. The numerical value of the perfusion 46 is displayed to the right of the bar elements 42, 44. Moreover, a symbol 48 indicates that corresponding alarm limits for the perfusion have been deactivated.

Whereas the bar element 42 symbolizes the reference value so that the length of the bar element 42 is constant, the bar element 44 represents, by way of its variable length, the variation of the perfusion in relation to the reference value. The fact that the length of the bar element 44 is variable is denoted by the dashed line 50.

The variation of the perfusion can then be readily and intuitively read out by the clinical staff via the different bar length. In order to ensure optimum presentation, the bar elements 42, 44 can be scaled, that is, the length of the bar element 42 can be individually adjusted, causing a corresponding variation of the length of the bar element 44.

The additional display of the estimate of the signal quality as derived by evaluation of various parameters such as the transmission level, interference level, artifact level, signal waveform and perfusion index, is realized by way of corresponding coloring of the bar elements 42, 44 shown. For example, a green bar element indicates a good signal quality while a yellow element indicates a dubious signal quality and a red bar element indicates a poor signal quality.

FIG. 4 shows a further possibility for the representation of the signal quality. FIG. 4 again concerns a part of a user surface 10 as used in the field of patient monitoring. The user surface 10 again displays the plethysmography curve 16, the $SPO_2$ value 20 with alarm limits 22 and the bar elements 42, 44 for presenting the variation of the perfusion with the associated numerical value 46. Three circular elements 52 are arranged horizontally adjacent one another as graphic elements for the presentation of the signal quality, that is, underneath the numerical value 46 of the perfusion. The signal quality is indicated in known manner by way of corresponding coloring of the circular elements, that is, green=good signal quality, yellow=mediocre signal quality, and red=poor signal quality.

FIG. 5 shows a further version in which only the variation of the perfusion is represented via the element 44, 50 in addition to the numerical information 20, 22 and 46 so that more room is available for the display of the plethysmography curve 16. The reference value is indicated by way of a further graphic element 54, for example, the tip of an arrow or a line.

LIST OF REFERENCES 10 user surface for patient monitoring
12 ECG curve, derivative I
14 ECG curve, derivative II
16 plethysmography curve
18 $CO_2$ respiration curve
20 $SPO_2$ value
22 alarm limits
24 measuring cap
26 first light-emitting diode
28 second light-emitting diode
30 photoreceiver
32 finger cap
34 tissue
36 arteries
38 veins
40 capillaries
42 first bar element
44 second bar element
46 numerical value of the perfusion
48 symbol for deactivated alarm limits
50 variation of the length of the second bar element
52 independent graphic elements for indicating the signal quality
54 marking of the reference value

The invention claimed is:

1. A method for the presentation of information concerning variations of the arterial filling with blood of organs of living beings on a display unit, the method comprising:
   determining perfusion index data for presentation using an algorithm from measured values produced by a non-invasive photometric measuring process for determining the arterial oxygen saturation of the blood;
   defining a first perfusion index as a reference value selected from perfusion index values determined during the photometric measuring process;
   determining subsequent perfusion indices as relative deviations with respect to the reference value;
   displaying the reference value on the display unit; and presenting said relative deviations as information concerning the variations of the perfusion on the display unit using first and second parallel bar elements for the presentation of the reference value and the relative deviations, respectively, where a length of the first parallel bar element represents the reference value and a variable length of the second parallel bar element represents the relative deviations.

2. A method as claimed in claim 1, wherein the defining of the reference value takes place automatically at the beginning of the photometric measuring process.

3. A method as claimed in claim 1, wherein the reference value is stored on a memory chip.

4. A method as claimed in claim 1, wherein the reference value as well as the subsequent perfusion indices are scaled by a factor.

5. A method as claimed in claim 4, wherein the factor is adjustable.

6. A method as claimed in claim 1, wherein the relative deviation of the perfusion is further presented in numerical form and the reference value is displayed in numerical form.

7. A method as claimed in claim 1, wherein the display is formed as a multidimensional type in conjunction with other physiological variables.

8. A method as claimed in claim 1, wherein an upper alarm limit and a lower alarm limit are provided.

9. A method as claimed in claim 8, wherein the alarm limit is adjustable.

10. A method as claimed in claim 8, wherein an alarm signal is triggered when the alarm limit is exceeded.

11. A device comprising:
a pulsoximeter for determining arterial $O_2$ saturation and for providing perfusion data; and
a display unit configured to display:
a first parallel bar graphical element whose length is indicative of a reference perfusion index value derived from the provided perfusion data at a reference time,
a second parallel bar graphical element whose length is indicative of a subsequent perfusion index value derived from the provided perfusion data at a subsequent time, and
arterial $O_2$ saturation determined by the pulsoximeter, wherein the display unit displays the first and second parallel bar graphical elements together to provide a visual indication of a relative deviation of the subsequent perfusion index value from the reference perfusion index value.

* * * * *